United States Patent [19]

Klaus et al.

[11] Patent Number: 5,128,470

[45] Date of Patent: Jul. 7, 1992

[54] AROMATIC CARBOXAMIDES

[75] Inventors: Michael Klaus, Weil am Rhein, Fed. Rep. of Germany; Peter Mohr, Basel, Switzerland

[73] Assignee: Hoffmann-La Roche Inc., Nutley, N.J.

[21] Appl. No.: 551,831

[22] Filed: Jul. 12, 1990

[30] Foreign Application Priority Data

Jul. 28, 1989 [CH] Switzerland ................ 2818/89

[51] Int. Cl.⁵ ............... C07C 233/75; C07C 233/66; C07D 295/15
[52] U.S. Cl. ................. 544/165; 544/400; 564/180; 564/184
[58] Field of Search ............ 564/180, 184; 544/165, 544/400

[56] References Cited

U.S. PATENT DOCUMENTS

| | | | |
|---|---|---|---|
| 4,511,581 | 4/1985 | Ohsumi et al. | 514/617 |
| 4,578,498 | 3/1986 | Frickel et al. | 560/8 |
| 4,703,110 | 10/1987 | Shudo | 534/566 |
| 4,808,631 | 2/1989 | Klaus | 514/561 |
| 4,927,928 | 5/1990 | Shroot et al. | 544/154 |
| 4,992,576 | 2/1991 | Gapinski | 560/52 |

FOREIGN PATENT DOCUMENTS

| | | |
|---|---|---|
| 0253503 | 1/1988 | European Pat. Off. |
| T/46296 | 1/1988 | Hungary |
| 1071843 | 3/1989 | Japan ........... 564/184 |

OTHER PUBLICATIONS

Chemical Abstracts 9th coll p. 19608cs RN 51932-71-9.
Royer, Bull Soc Shim France 1959 (1148) *Abstract*.
El'mesov, Dokl. AKAD NAUK SSSR 286 1453 (1986) *Abstract*.
Schlatter, ACS Div Petrol Chem Preprints Symposia 1 No. 2 77–82 (1956) *Abstract*.

*Primary Examiner*—Robert Gerstl
*Attorney, Agent, or Firm*—George M. Gould; William H. Epstein; Bruce A. Pokras

[57] ABSTRACT

Compounds of the general formula

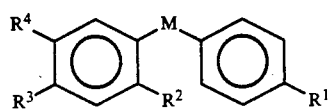

I wherein $R^1$ is hydrogen, halogen or $OR^5$; $R^2$ is hydrogen, lower-alkyl, lower-alkoxy or halogen; $R^3$ and $R^4$ each independently are lower-alkyl or taken together are alkylene with 3–5 C atoms in a straight-chain; $R^5$ is hydrogen, acyl, lower-alkoxycarbonyl, lower-alkyl, amino-lower-alkyl, mono-alkylamino-lower-alkyl, di-alkylamino-lower-alkyl or a N-containing 5-8-membered saturated or unsaturated monocyclic heterocyclic ring which is attached via a N atom to lower alkyl; and M signifies —CONH— or —NHCO—, which can be used as medicaments, e.g., for the treatment of neoplasms and dermatological indications of an inflammatory and allergic nature.

34 Claims, No Drawings

AROMATIC CARBOXAMIDES

SUMMARY OF THE INVENTION

The present invention is concerned with novel aromatic carboxamides of the general formula

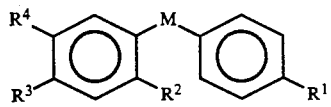

wherein $R^1$ is hydrogen, halogen or $OR^5$; $R^2$ is hydrogen, lower-alkyl, lower-alkoxy or halogen; $R^3$ and $R^4$ each independently are lower-alkyl or taken together are alkylene with from 3 to 5 carbon atoms in a straight-chain; $R^5$ is hydrogen, acyl, lower-alkoxycarbonyl, lower-alkyl, amino-lower-alkyl, mono-alkylamino-lower-alkyl, di-alkylamino-lower-alkyl, or a nitrogen-containing 5 to 8 membered, saturated or unsaturated monocyclic heterocyclic ring attached via a nitrogen atom to lower alkyl; and M is —CONH— or —NH-CO—.

The invention also comprises a process for the manufacture of the compounds of formula I, pharmaceutical preparations based on the compounds of formula I, especially for the treatment and prophylaxis of neoplasms, dermatoses and aging of the skin, rheumatic and immunological disorders, as well as methods for the manufacture of pharmaceutical preparations containing compounds of formula I for the treatment and prophylaxis of such disorders.

DETAILED DESCRIPTION OF THE INVENTION.

The term "lower" relates to groups with 1-6 C atoms Alkyl and alkoxy groups can be straight-chain or branched, such as methyl, ethyl, propyl isopropyl, butyl, sec-butyl or tert-butyl and, respectively, methoxy, ethoxy, propoxy, isopropoxy, butoxy, sec-butoxy and tert-butoxy. Examples of acyl groups are alkanoyl groups, preferably lower-alkanoyl groups such as acetyl, propionyl, butyryl, pivaloyl and caproyl; or aroyl groups such as benzoyl, p-nitrobenzoyl and toluoyl; or aralkanoyl groups such as phenylacetyl.

Preferred heterocyclic rings are those of the formula

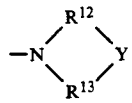

in which Y is —CH$_2$—, —CH=, —O—, —S—, —SO—, —SO$_2$— or —NR$^6$— and $R^6$ is hydrogen, lower-alkyl or acyl and in which $R^{12}$ and $R^{13}$ are the same or different and are straight chained alkylene containing up to 6 carbon atoms with the proviso that $R^{12}$ and $R^{13}$ contain a total of 3 to 6 carbon atoms piperidino, pyrrolidino, morpholino, piperazino, N-methylpiperazino, thiomorpholino, thiomorpholino 4-oxide, thiomorpholino 4,4-dioxide as well as imidazolino and pyrrolo are examples of such rings.

When $R^5$ is amino-lower-alkyl, mono-alkylamino-lower-alkyl, or di-alkylamino-lower-alkyl, $R^5$ has the formula:

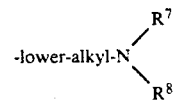

wherein $R^7$ and $R^8$ are independently hydrogen or lower-alkyl.

An alkylene residue with from 3 to 5 carbon atoms in a straight chain represented by $R^3$ and $R^4$ together can have branchings. Examples of the alkylene groups are 1,3-propylene, 1,4-butylene and 1,5-pentylene and lower-alkyl-substituted derivatives thereof such as the groups —C(CH$_3$)$_2$—CH$_2$—C(CH$_3$)$_2$—, —C(CH$_3$)$_2$—CH$_2$CH$_2$—C(CH$_3$)$_2$— and —CH$_2$CH$_2$—C(CH$_3$)$_2$—CH$_2$CH$_2$—.

$R^1$ is preferably hydrogen, hydroxy, fluorine, morpholinoethoxy or N-methylpiperidinoethoxy.

Among the preferred compounds are compounds of the formula:

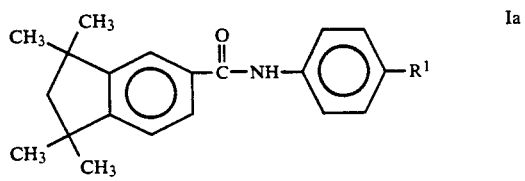

Ia

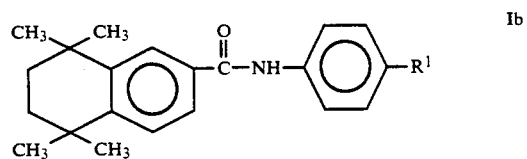

Ib

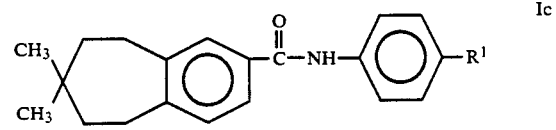

Ic

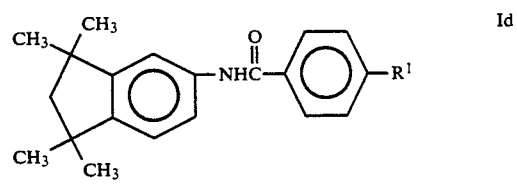

Id

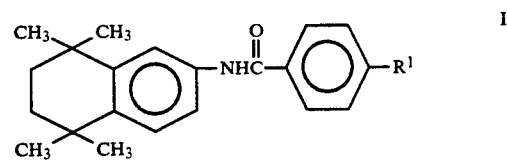

Ie

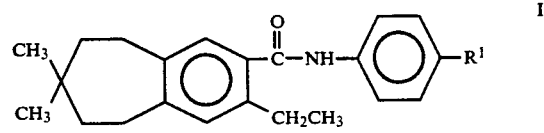

If

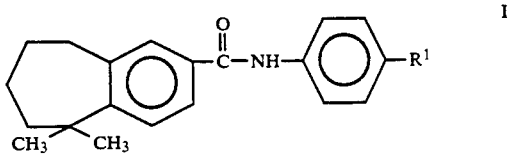

Ig

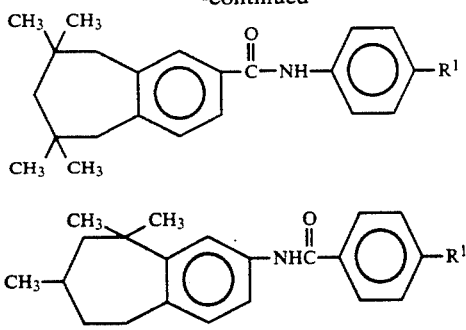

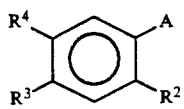

The compounds of formula I can be obtained by reacting a compound of the general formula

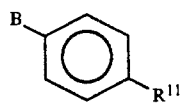

with a compound of the general formula

III wherein either A signifies a carboxyl group or a reactive derivative thereof and B signifies an amino group or A signifies an amino group and B signifies a carboxyl group or a reactive derivative thereof and $R^{11}$ signifies a group $R^1$ in which an amino group which may be present is in protected form, whereupon an amino protecting group which may be present is cleaved off.

The reaction of a compound II with a compound III can be carried out according to methods known for the acylation of amines. Preferably, a compound of formula II in which A is a carboxylic acid halide group, e.g., the group —COCl is reacted with a compound of formula III in which B is —NH$_2$ to give a compound of formula I in which M is —CONH—, or an amine of formula II is reacted with a carboxylic acid halide of formula III to give a compound of formula I in which M is —NH—CO—.

These acylations are conveniently carried out in the presence of a base, e.g., an organic base such as pyridine.

Conventional amino protecting groups such as the phthaloyl group, the benzyloxycarbonyl group and the tert-butoxycarbonyl group may be used as amino protecting groups. The cleavage of these protecting groups can be effected with conventional agents. A phthaloyl group can be cleaved off by treatment with hydrazine; a benzyloxycarbonyl group can be cleaved off by catalytic hydrogenation; and a tert-butoxycarbonyl group can be cleaved off by treatment with acids, e.g., dilute hydrochloric acid or trifluoroacetic acid.

The compounds of formulas II and III which are used as starting materials for the manufacture of the compounds of formula I, insofar as they are not known or described hereinafter, can be prepared by known methods or the methods described hereinafter.

The compounds of formula I are pharmacodynamically valuable compounds. They can be used for the topical and systemic therapy of benign and malignant neoplasms and premalignant lesions, and also for the systemic and topical prophylaxis of the said conditions.

The compounds of formula I are suitable for the topical and systemic therapy of acne, psoriasis and other dermatoses which are accompanied by an intensified or pathologically altered cornification, inflammatory and allergic dermatological conditions, and light-damaged (aged) skin. Further, the compounds of formula I can also be used for the control of mucous membrane disorders with inflammatory or degenerative or metaplastic changes. The antineoplastic activity of the compounds of formula I can be investigated using the following test procedure:

Female Sprague-Dawley rats are held under temperature-controlled and light-controlled conditions with free access to drinking water and feed. At the age of 50 days 12 mg of 7,12-dimethylbenz(a)anthracene are administered to each rat by means of a stomach tube. After a period of about 4 months, in which on average 3.6 to 4 mammary tumors have developed per rat, the treatment is commenced. The test substance is admixed with normal feed in a 25% spray-dried formulation. The following parameters are measured weekly: body weight, average number of tumors and average tumor volume per animal. The volumes are calculated according to the formula $D/2 \cdot d^2$ in which D is the largest diameter of the tumor ellipsoid and d is the smallest diameter of the tumor ellipsoid.

The values obtained with the compound of Example 3 in this test procedure after a test period of 10 weeks are presented in Table I:

TABLE I

| Dosage [mg/kg/day] p.o. | Change in the average number of tumors per rat [%] | Change in the average tumor volume per rat [%] |
| --- | --- | --- |
| 50 | +50 | +840 |
| 100 | +35 | +475 |
| 200 | +16 | +193 |
| Control group | +78 | +875 |

The compounds of formula I can also be used for the treatment of inflammatory, allergic, rheumatic and immunological disorders of the widest variety of organs. Examples of such disorders are: primary-chronic polyarthritis, spondylarthritis ancylopoetica, osteoarthritides, arthritides and arthroses; eczemas, atopic dermatitis, allergic rhinitis, bronchial asthma; autoimmune disorders such as e.g. lupus erythematosus, Reiter's syndrome.

The compounds of formula I can accordingly be used as medicaments, e.g. in the form of pharmaceutical preparations.

The preparations can be administered enterally, parenterally or topically, preparations in the form of tablets, capsules, dragees, syrups, suspensions, solutions and supposirories are suitable e.g. for parenteral administration. Preparations in the form of infusion solutions or injection solutions are suitable for parenteral administration.

The dosages in which the preparations are administered can vary according to the mode of use and route of use as well as according to the requirements of the patients. For oral administration of the compounds in accordance with the invention, adults dosages of about 0.1-100 mg/kg, preferably 0.5-50 mg/kg, per day may be used.

The preparations can be administered in one dosage or several dosages. Capsules containing about 5–500 mg of active ingredient are a preferred administration form.

The preparations can contain inert or also pharmacodynamically active additives. Tablets or granulates e.g. can contain a series of binding agents, filler materials, carrier substances or diluents. Liquid preparations can be present, for example, in the form of a sterile solution which is miscible with water. Capsules can additionally contain a filler material or thickening agent in addition to the active ingredient. Furthermore, there can also be present flavor-improving additives as well as the substances usually used as preserving, stabilizing, moisture-retaining and emulsifying agents. In addition, salts for varying the osmotic pressure, buffers and other additives may be included.

The previously mentioned carrier substances and diluents can consist of organic or inorganic substances, e.g., water, gelatin, lactose, starch magnesium stearate, talc, gum arabic, polyalkylene glycols and the like. It is a prerequisite that all adjuvants used in the manufacture of the preparations are non-toxic.

For topical use the active ingredients are conveniently used in the form of salves, tinctures, creams, solutions, lotions, sprays, suspensions and the like. Salves and creams as well as solutions are preferred. The preparations intended for topical use can be prepared by mixing the process products as active ingredients with non-toxic, inert, solid or liquid carriers which are known to be useful in such preparations and which are suitable for topical treatment.

For topical use, solutions, salves or creams containing about 0.1%–5%, preferably 0.3%–2%, of the compounds of the present invention may be used.

If desired, an antioxidant e.g., tocopherol, N-methyl-Y-tocopheramine as well as t-butyl-hydroxyanisole or t-butyl-hydroxytoluene, can be admixed with the preparations.

EXAMPLE 1

2 g of 5,6,7,8-tetrahydro-5,5,8,8-tetramethyl-2-naphthalenecarboxylic acid were treated with 15 ml of thionyl chloride and heated at reflux for 1 hour. After distilling of the excess thionyl chloride the residue was dissolved in 10 ml of tetrahydrofuran and added dropwise while stirring to a solution of 0.9 g of aniline in 20 ml of pyridine. After stirring at room temperature for half an hour the reaction mixture was poured on to ice-water, extracted with ethyl acetate, the organic phase was washed with 2N hydrochloric acid and water, dried and evaporated. The orange-colored oil was crystallized from hexane and gave 1.8 g of 5,6,7,8-tetrahydro-5,5,8,8-tetramethyl-2-naphthalenecarboxanilide in colorless crystals, m.p. 144° C.–146° C.

EXAMPLE 2

In a manner analogous to Example 1, 2 g of 5,6,7,8-tetrahydro-5,5,8,8-tetramethyl-2-naphthalene-carboxylic acid and 1 g of 4-fluoroaniline were used to obtain 1.7 g of 4'-fluoro-5,6,7,8-tetrahydro-5,5,8,8-tetramethyl-2-naphthalenecarboxanilide in colorless crystals. m.p. 163° C.–165° C. (from ethyl acetate/hexane).

EXAMPLE 3

In a manner analogous to Example 1, 52.5 g of 5,6,7,8-tetrahydro-5,5,8,8-tetramethyl-2-naphthalene-carboxylic acid were converted by reaction with 200 ml of thionyl chloride into the acid chloride and, after dissolution in 200 ml of tetrahydrofuran, added dropwise to a solution of 48.8 g of 4-[2-(4-amino-phenoxy)ethyl]-morpholine in 400 ml of pyridine while cooling slightly. The temperature should not rise above 30° C. After stirring at room temperature for 1 hour the reaction mixture was poured on to ice-water, extracted with ethyl acetate, the organic phase was washed with ice-cold 2N hydrochloric acid, dried and evaporated. The crystalline crude product was purified by filtration over a silica gel column (eluting agent hexane/ethyl acetate 1:4, then ethyl acetate, then ethyl acetate/ethanol =1:1) and recrystallized from hexane/ ethyl acetate. There were obtained 52 g of 5,6,7,8-tetrahydro-5,5,8,8-tetramethyl-4'-(2-morpholinoethoxy)-2-naphthalenecarboxanilide in white crystals. m.p. 134° C.–136° C.

The 4-[2-(4-amino-phenoxy)ethyl]morpholine used as the starting material was prepared as follows:

19 g of sodium hydride (50% suspension in mineral oil) were washed twice with absolute pentane, dried and suspended in 130 ml of dimethylformamide. A solution of 42.5 g of 4-aminophenol in 250 ml of dimethylformamide was added dropwise thereto while cooling with ice and the mixture was stirred at 0° C. for a further hour. Thereafter, a solution of 100 g of 4-(2-chloro-ethyl)-morpholine in 250 ml of dimethylformamide was added dropwise thereto. After heating to 70° C. for 1 hour the reaction mixture was poured on to ice-water, extracted with ethyl acetate, the organic phase was washed with water, dried and evaporated. The thus-obtained dark brown oil was purified by filtration over a silica gel column (eluting agent ethyl acetate) and, after drying in a high vacuum, gave 66 g of 4-[2-(4-aminophenoxy)ethyl]morpholine as a slightly brownish oil.

EXAMPLE 4

In a manner analogous to Example 1, 2 g of 5,6,7,8-tetrahydro-5,5,8,8-tetramethyl-2-naphthalene-carboxylic acid and 0.95 g of 4-aminophenol were reacted to obtain, after recrystallization from hexane/ethyl acetate, 2.1 g of 5,6,7,8-tetrahydro-5,5,8,8-tetramethyl-4'-hydroxy-2-naphthalenecarboxanilide in beige crystals, m.p. 216° C.–218° C.

EXAMPLE 5

In a manner analogous to Example 1, 4 g of 1,1,3,3-tetramethyl-5-indanecarboxylic acid and 1.7 g of aniline were reacted to obtain, after recrystallization from hexane/ethyl acetate, 3.3 g of 1,1,3,3-tetramethyl-5-indanecarboxanilide in white crystals, m.p. 137° C.–138° C.

EXAMPLE 6

In a manner analogous to Example 1, 4 g of 1,1,3,3-tetramethyl-5-indanecarboxylic acid and 2 g of 4-fluoroaniline were reacted to obtain, after recrystallization from hexane/ ethyl acetate. 2.1 g of 4'-fluoro-1,1.3,3-tetramethyl-5- -indanecarboxanilide. m.p. 155° C.–156° C.

EXAMPLE 7

In a manner analogous to Example 3, the reaction of 5.7 g of 1,1,3,3-tetramethyl-5-indanecarboxylic acid with 5.8 g of 4-[2-(4-aminophenoxy)ethyl]morpholine gave, after recrystallization from hexane/ethyl acetate. 5.2 g of 1,1,3,3-tetramethyl-4'-(2-morpholinoethoxy)-5-indanecarboxanilide in white crystals, m.p. 131° C.–133° C.

EXAMPLE 8

In a manner analogous to Example 1, 4 g of 1,1,3,3-tetramethyl-5-indanecarboxylic acid and 1.9 g of 4-aminophenol were reacted to obtain, after recrystallization from hexane/ ethyl acetate, 2.3 g of 4'-hydroxy-1,1,3.3-tetramethyl-5-indanecarboxanilide, m.p. 196° C.–197° C.

EXAMPLE 9

2.5 g of 5,6,7,8-tetrahydro-5,5,8,8-tetramethyl-2-naphthylamine were dissolved in 50 ml of pyridine and treated at room temperature with a solution of 1.7 g of benzoyl chloride in 20 ml of tetrahydrofuran. After stirring at room temperature for two hours the reaction mixture was poured on to ice-water and, after acidification with 3N hydrochloric acid, extracted with ethyl acetate. The oil obtained after drying and evaporating the organic phase was crystallized from hexane/ethyl acetate and gave 3 g of N-(5,6,7,8-tetrahydro-5,5,8.8-tetramethyl-2-naphthyl)benzamide in white crystals, m.p. 146° C.–148° C.

EXAMPLE 10

In a manner analogous to Example 9, by reacting 5.9 g of 5,6,7,8-tetrahydro-5,5,8,8-tetramethyl-2-naphthylamine with 4-fluorobenzoyl chloride, obtained from 4 g of 4-fluorobenzoic acid and 15 ml of thionyl chloride, there were obtained, after recrystallization from hexane/ethyl acetate, 6.3 g of p-fluoro-N-(5,6,7,8-tetrahydro-5,5,8,8-tetramethyl-2-naphthyl)benzamide, m.p. 160° C.–162° C.

EXAMPLE 11

6.1 g of p-(2-morpholinoethoxy)benzoic acid were covered with 100 ml of thionyl chloride and heated at reflux for 1 hour. After evaporating the excess thionyl chloride the residue was suspended in 100 ml of tetrahydrofuran and added dropwise to a solution of 4.9 g of 5,6,7,8-tetrahydro-5,5,8,8-tetramethyl-2-naphthylamine in 150 ml of pyridine. After stirring at room temperature for 20 hours the reaction mixture was poured on to ice-water and extracted with ethyl acetate. After repeatedly washing the organic phase with water, drying over sodium sulphate and evaporating the solvent there was obtained a crystalline crude product which was purified by filtration over a silica gel column (eluting agent hexane/ethyl acetate =1:1, then ethyl acetate) and crystallization from hexane/ethyl acetate. There were obtained 8.6 g of p-(2-morpholinoethoxy)-N-(5,6,7,8-tetrahydro-5,5,8,8-tetramethyl-2-naphthyl)benzamide, m.p. 130° C.–132° C.

The p-(2-morpholinoethoxy)benzoic acid used as the starting material was prepared as follows:

10 g of methyl 4-hydroxybenzoate and 20.5 g of 4-(2-chloroethyl)morpholine were dissolved in 100 ml of dimethylformamide and, after the addition of 38 g of potassium carbonate, heated to 100° C. for 1 hour. The reaction mixture obtained was poured on to ice-water, extracted with ethyl acetate, dried and evaporated. The oily, slightly brown residue was saponified with potassium hydroxide in water/ethanol and, after acidification and recrystallization from hexane/ ethyl acetate, gave 7.3 g of p-(2-morpholinoethoxy)benzoic acid in beige crystals. m.p. 112° C.–114° C.

EXAMPLE 12

In a manner analogous to Example 9, 1 g of 5,6,7,8-tetrahydro-5,5,8,8-tetramethyl-2-naphthylamine and 1 g of p-acetoxybenzoyl chloride were reacted to obtain after recrystallization from hexane/ethyl acetate, 1.5 g of p-[(5,6,7,8-tetrahydro-5,5,8,8-tetramethyl-2-naphthyl)carbamoyl]phenyl acetate. m.p. 186° C.–188° C.

Hydrolysis of this compound with potassium hydroxide/ water/ethanol gave, after recrystallization from hexane/ ethyl acetate, 1.1 g of p-hydroxy-N-(5.6,7,8-tetrahydro-5,5,8,8-tetramethyl-2-naphthyl)benzamide, m.p. 204° C.–206° C.

EXAMPLE 13

In a manner analogous to Example 9, 2.5 g of 1,1,3.3-tetramethyl-5-indanamine and 1.9 g of benzoyl chloride were reacted to obtain, after recrystallization from hexane/ethyl acetate, 2.7 g of N-(1,1,3,3-tetramethyl-5-indanyl)benzamide, m.p. 167° C.–169° C.

EXAMPLE 14

In a manner analogous to Example 9, 5.5 g of 1,1,3,3-tetramethyl-5-indanamine and 4 g of 4-fluorobenzoyl chloride were reacted to obtain, after recrystallization from hexane/ ethyl acetate, 5.5 g of p-fluoro-N-(1,1,3,3-tetramethyl-5-indanyl)benzamide, m.p. 167° C.–169° C.

EXAMPLE 15

In a manner analogous to Example 11. 4 g of p-(2-morpholinoethoxy)benzoic acid and 3.1 g of 1,1.3,3-tetramethyl-5-indanamine were reacted to obtain, after recrystallization from hexane/ethyl acetate, 4.6 g of p-(2-morpholinoethoxy)-N-(1.1,3,3-tetramethyl-5-indanyl)benzamide, m.p. 134° C.–136° C.

EXAMPLE 16

In a manner analogous to Example 12, 2 g of 1,1,3,3-tetramethyl-5-indanamine and 2.2 g of p-acetoxybenzoyl chloride were reacted to obtain, after recrystallization from hexane/ ethyl acetate. 2.7 g of p-[1.1,3,3-tetramethyl-5-indanoyl]carbamoyl]phenyl acetate, m.p. 196° C.–198° C.

Hydrolysis of this compound gave 2.2 g of p-hydroxy-N-(1,1,3,3-tetramethyl-5-indanyl)benzamide, m.p. 185° C.–187° C.

EXAMPLE 17

1.77 g of 6,7,8,9-tetrahydro-7,7-dimethyl-5H-benzocycloheptene-2-carboxylic acid were treated with 1.17 ml of SOCl₂ and heated to reflux for ¾ hour. The excess reagent was removed under reduced pressure and the crude acid chloride was dried briefly in a high vacuum. It was then dissolved in 20 ml of abs. pyridine and added dropwise under an argon atmosphere at 0° C. to a solution of 0.97 g of 4-aminophenol in 16 ml of abs. pyridine. The mixture was left to react at room temperature for 20 minutes and then poured on to ice/conc. HCl. The mixture was then extracted with ethyl acetate, washed with 1N HCl. 10% sodium carbonate solution and saturated NaCl solution, dried over Na₂SO₄, boiled with active charcoal and filtered. The filtrate was concentrated under reduced pressure until the product began to crystallize and there were obtained 1.98 g of 6,7,8,9-tetrahydro-7,7-dimethyl-5H-benzocycloheptene-2-carboxylic acid (4-hydroxy)anilide as brownish crystals of melting point 175° C.–176° C.

The educt can be prepared as follows:

A mixture of 11.4 g of K₂CO and 3.40 g of KOH dissolved in 30 ml of H₂O was added to 16.3 g of Ca-(OCl)₂ in 60 ml of H₂O. The mixture was stirred intensively for ¼ hour and then filtered. 6.49 g of 6,7,8,9-tetrahydro-7,7-dimethyl-5H-benzocyclohepten-2-yl methyl ketone were added to the filtrate (calcium hypochlorite) and the mixture was heated slowly. A strongly exothermic reaction occurred at 70° C. and this allowed the temperature to rise to 100° C. After cooling the mixture was acidified cautiously with 50 ml of 3N HCl and the precipitated acid was filtered off. After washing with H₂O and drying in a high vacuum there were obtained 5.48 g of 6,7,8,9-tetrahydro-7,7-dimethyl-5H-benzocyclo-heptene-2-carboxylic acid as white crystals of melting point 166° C.–171° C.

EXAMPLE 18

In a manner analogous to Example 17, but using 4-fluoroaniline as the amine component, there was manufactured 6,7,8,9-tetrahydro-7,7-dimethyl-5H-benzocycloheptene-2-carboxylic acid (4-fluoro)anilide as white crystals of melting point 178° C.–179° C.

EXAMPLE 19

In a manner analogous to Example 17, but using aniline as the amine component, there was manufactured 6,7,8,9-tetrahydro-7,7-dimethyl-5H-benzocycloheptene-2-carboxylic acid anilide as white crystals of melting point 146° C.–147° C.

EXAMPLE 20

In a manner analogous to Example 17, 4-aminophenol and 6.7,8,9-tetrahydro-9,9-dimethyl-5H-benzocycloheptene-2-carboxylic acid were reacted to obtain 6,7,8,9-tetrahydro-9,9-dimethyl-5H-benzocycloheptene-2-carboxylic acid (4-hydroxy)anilide as white crystals of melting point 147° C.–148° C.

The starting material can be prepared as follows:

The Grignard compound was prepared under an argon atmosphere from 4.00 g of 2-bromo-6,7,8,9-tetrahydro-9,9--dimethyl-5H-benzocycloheptene, as described in EP-A2-0315071, and 456 mg of Mg shavings in 20 ml of absolute tetrahydrofuran. After carrying out the metallation a vigorous CO₂ stream was introduced at −10° C. The mixture was hydrolyzed with dil. HCl, extracted with ether and washed with a small amount of water. The acid was then purified by extraction in 1N NaOH, acidification to pH 1 (HCl) and re-extraction in ether. After washing with water, drying over Na₂SO₄ and evaporating there were obtained 2.64 g of 6,7,8,9--tetrahydro-9,9-dimethyl-5H-benzocycloheptene-2-carboxylic acid as colorless crystals of melting point 155° C.–156° C.

EXAMPLE 21

In a manner analogous to Example 17, 4-fluoroaniline and 6,7,8,9-tetrahydro-9,9-dimethyl-5H-benzocycloheptene-2-carboxylic acid were reacted to obtain 6,7,8,9-tetrahydro-9,9-dimethyl-5H-benzocycloheptene-2-carboxylic acid (4-fluoro)anilide as colorless crystals of melting point 135° C.–136° C.

EXAMPLE 22

In a manner analogous to Example 17, 3-ethyl6,7,8,9-tetrahydro-7,7-dimethyl-5H-benzocyclohepten-2-yl methyl ketone and 4-aminophenol were reacted to obtain 3-ethyl-6,7,8,9-tetrahydro-7,7-dimethyl-5H-benzocycloheptene-2-carboxylic acid (4-hydroxy)anilide as colorless crystals of melting point 197° C.–198° C.

The starting material can be synthesized from ethylbenzene. 3,3-dimethylglutaric anhydride and acetyl chloride by the procedure described in EP-A2-0315071.

EXAMPLE 23

The following compounds can be manufactured in a manner analogous to Example 1:

6,7,8,9-Tetrahydro-7,7-dimethyl-4'-[2-(4-methylpiperazino)ethoxy]-(5H)-benzocycloheptene-2-carboxanilide;

6,7 8,9-tetrahydro-4'-hydroxy-5,5-dimethyl-5H-benzocycloheptene-2-carboxanilide;

4'-[2-[bis(2-methoxyethyl)amino]ethoxy]-6,7,8,9-tetrahydro-6,6,8,8-tetramethyl-5H-benzocycloheptene-2-carboxanilide;

5.6,7,8-tetrahydro-5,5,8,8-tetramethyl-4'-[2-(4-methylpiperazino)ethoxy]-2-naphthalenecarboxanilide;

1.1,3,3-tetramethyl-4'-(2-dimethylaminoethoxy)-5-indanecarboxanilide.

EXAMPLE 24

The following compounds can be manufactured in a manner analogous to Example 9:

p-Fluoro-N-(6,7,8,9-tetrahydro-7,9,9-trimethyl-5H-benzocyclohepten-2-yl)benzamide;

p-(2-imidazoloethoxy)-N-(5,6,7,8-tetrahydro-5,5,8,8-tetramethyl-2-naphthyl)benzamide;

p-(2-morpholinoethoxy)-N-(6,7,8,9-tetrahydro-7,7-dimethyl-5H-benzocyclohepten-2-yl)benzamide;

6,7,8,9-tetrahydro-7,7-dimethyl-4'-[2-(4-methylpiperazino)ethoxy]-(5H)-2-benzocycloheptenecarboxanilide.

EXAMPLE 25

Hard gelatin capsules can be manufactured as follows:

| Ingredients | mg/capsule |
| --- | --- |
| 1. Spray-dried powder containing 75% of compound I | 200 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 300 |

The spray-dried powder, which is based on the active ingredient gelatin and microcrystalline cellulose and which has an average particle size of the active ingredient of <1 μ (measured by means of autocorrelation spectroscopy). is moistened with an aqueous solution of sodium carboxymethylcellulose and sodium dioctylsulphosuccinate and kneaded. The resulting mass is granulated, dried and sieved, and the granulate obtained is mixed with microcrystalline cellulose, talc and magnesium stearate. The powder is filled into size 0 capsules.

EXAMPLE 26

Tablets can be manufactured as follows:

| Ingredients | mg/tablet |
| --- | --- |
| 1. Compound I as a finely milled powder | 500 |
| 2. Powd. lactose | 100 |
| 3. White maize starch | 60 |

-continued

| Ingredients | mg/tablet |
| --- | --- |
| 4. Povidone K30 | 8 |
| 5. White maize starch | 112 |
| 6. Talc | 16 |
| 7. Magnesium stearate | 4 |
| Total | 800 |

The finely milled substance is mixed with lactose and a portion of the maize starch. The mixture is moistened with an aqueous solution of Povidone K30 and kneaded, and the resulting mass is granulated, dried and sieved. The granulate is mixed with the remaining maize starch, talc and magnesium stearate and pressed to tablets of suitable size.

EXAMPLE 27

Soft gelatin capsules can be manufactured as follows:

| Ingredients | mg/capsule |
| --- | --- |
| 1. Compound I | 50 |
| 2. Triglyceride | 450 |
| Total | 500 |

10 g of compound I are dissolved in 90 g of medium-chain triglyceride with stirring, inert gasification and exclusion from light. This solution is processed as a capsule fill mass to soft gelatin capsules containing 50 mg of active ingredient.

EXAMPLE 28

A lotion can be manufactured as follows:

| Ingredients | |
| --- | --- |
| 1. Compound I, finely milled | 3.0 g |
| 2. Carbopol 934 | 0.6 g |
| 3. Sodium hydroxide | q.s. ad pH 6 |
| 4. Ethanol, 94% | 50.0 g |
| 5. Demineralized water | ad 100.0 g |

The active ingredient is incorporated into the 94% ethanol/water mixture under protection from light. Carbopol 934 is stirred in until gelling is complete and the pH value is adjusted with sodium hydroxide.

We claim:

1. A compound of the general formula

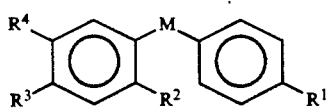

wherein $R^1$ is halogen or $OR^5$; $R^2$ is hydrogen, lower-alkyl, lower alkoxy or halogen; $R^3$ and $R^4$ taken together are alkylene with from 3 to 5 carbon atoms in a straight-chain wherein said straight-chain may be unsubstituted or substituted by lower-alkyl; $R^5$ is hydrogen, acyl, lower-alkoxycarbonyl, lower-alkyl, amino-lower-alkyl, mono-alkylamino-lower-alkyl, di-alkylamino-lower-alkyl, or a nitrogen-containing 5 to 8 membered, saturated or unsaturated monocyclic heterocyclic ring attached via a nitrogen atom to lower alkyl; and M is —CONH—.

2. The compound according to claim 1, wherein $R^3$ and $R^4$ taken together is —C(CH$_3$)$_2$—CH$_2$—C(CH$_3$)$_2$—, —C(CH$_3$)$_2$—CH$_2$CH$_2$—C(CH$_3$)$_2$— or —CH$_2$CH$_2$—C(CH$_3$)$_2$—CH$_2$CH$_2$—.

3. The compound of claim 1, wherein said compound has the formula

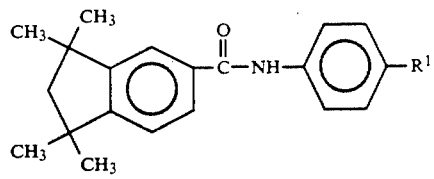

wherein $R^1$ is as above.

4. The compound of claim 3, wherein $R^1$ is halogen.

5. The compound of claim 4, wherein said compound is 4'-fluoro-1,1.3,3-tetramethyl-5-indanecarboxanilide.

6. The compound of claim 3, wherein said compound is 4'-hydroxy-1,1,3,3-tetramethyl-5-indanecarboxanilide.

7. The compound of claim 3, wherein $R^1$ is $OR^5$.

8. The compound of claim 3, wherein said compound is 3-tetramethyl-4'-(2-dimethylaminoethoxy)-5-indaneilide.

9. The compound of claim 7, wherein $R^5$ is a nitrogen-containing 5 to 8 membered saturated or unsaturated monocyclic heterocyclic ring which is attached via a nitrogen atom to lower alkyl.

10. The compound of claim 9, wherein said compound 1,3,3-tetramethyl-4'-(2-morpholinoethoxy)-5indanecarboxanilide.

11. The compound of claim 1, wherein said compound the formula:

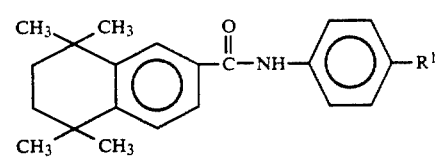

wherein $R^1$ is as above.

12. The compound of claim 11, wherein said compound is 6,7,8-tetrahydro-5,5.8,8-tetramethyl-2-naphthalenecarboxanilide.

13. The compound of claim 11, wherein $R^1$ is halogen.

14. The compound of claim 13, wherein said compound is 4'-fluoro-5,6,7,8-tetrahydro-5,5,8,8-tetramethyl-2-naphthalenecarboxanilide.

15. The compound of claim 11, wherein said compound is 5,6,7.8-tetrahydro-5,5,8,8-tetramethyl-4'-hydroxy-2-naphthalenecarboxanilide.

16. The compound of claim 11, wherein $R^1$ is $OR^5$.

17. The compound of claim 16, wherein $R^5$ is a nitrogen-containing 5 to 8 membered saturated or unsaturated monocyclic heterocyclic ring which is attached via a nitrogen atom to lower alkyl.

18. The compound of claim 16, wherein said compound is 5,6,7,8-tetrahydro-5,5,8.8-tetramethyl-4'-(2-morpholinoethoxy)-2-naphthalenecarboxanilide.

19. The compound of claim 16 wherein said compound is 5,6,7,8-tetrahydro-5,5,8,8-tetramethyl-4'-[2-(4-methylpiperazino)ethoxy]-2-naphthalenecarboxanilide.

20. The compound of claim 1, wherein said compound has the formula:

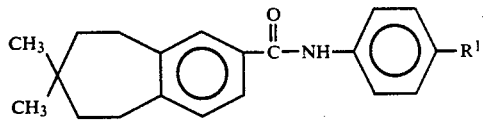

wherein R¹ is as above.

21. The compound of claim 20, wherein said compound is 6,7,8,9-tetrahydro-7,7-dimethyl-5H-benzocycloheptenenilide.

22. The compound of claim 20, wherein R¹ is halogen.

23. The compound of claim 20 wherein said compound is is 6,7,8,9-tetrahydro-7,7-dimethyl-5H-benzocycloheptene-2-carboxylic acid (4-fluoro)anilide.

24. The compound of claim 20 wherein said compound is is 6,7,8,9-tetrahydro-7,7-dimethyl-5H-benzocycloheptene-2-carboxylic acid (4-hydroxy)anilide.

25. The compound of claim 20 wherein R¹ is OR⁵.

26. The compound of claim 25 wherein R⁵ is a nitrogen-containing 5 to 8 membered saturated or unsaturated monocyclic heterocyclic ring which is attached via a nitrogen atom to lower alkyl.

27. The compound of claim 26, wherein said compound 6,7,8,9-tetrahydro-7,7-dimethyl-4'-[2-(4-methylpiperazino)ethoxyl]-(5H)-benzocycloheptene-2-carboxanilide.

28. The compound of claim 26, wherein said compound is 6,7,8,9-tetrahydro-7,7-dimethyl-4'-[2-(4-methylpiperazino)ethoxyl]-(5H)-benzocycloheptenecarboxanilide.

29. The compound of claim 1, wherein said compound has the formula:

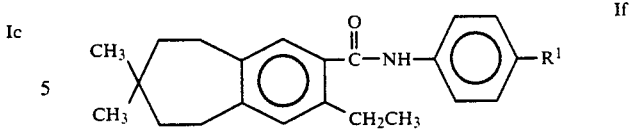

wherein R¹ is as above.

30. The compound of claim 29, wherein said compound is 3-ethyl-6,7,8,9-tetrahydro-7,7-dimethyl-5H)-benzocycloheptene-2-carboxylic acid (4-hydroxy)anilide.

31. The compound of claim 1, wherein said compound has the formula:

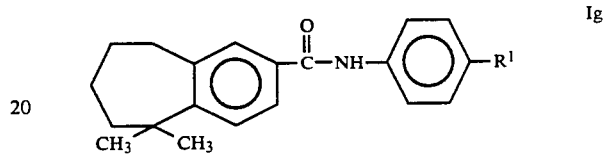

wherein R¹ is as above.

32. The compound of claim 31, wherein said compound is 6,7,8,9-tetrahydro-4'-hydroxy-5,5-dimethyl-5H)-benzocycloheptene-2-carboxanilide.

33. The compound of claim 1, wherein said compound has the formula:

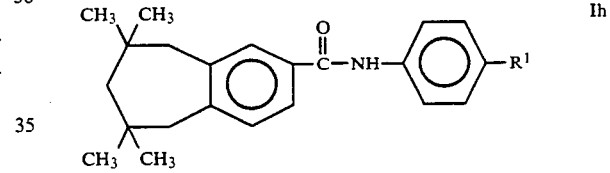

wherein R¹ is as above.

34. The compound of claim 33, wherein said compound is 4'-[bis(2-methoxyethyl)amino]ethoxy]-6,7,8,9-tetrahydro-6,6,8,8-tetramethyl-5H-benzocycloheptene-2-carboxylicanilide.

* * * * *

UNITED STATES PATENT AND TRADEMARK OFFICE
CERTIFICATE OF CORRECTION

PATENT NO. : 5,128,470
DATED : July 7, 1992
INVENTOR(S) : Michael Klaus, Peter Mohr It is certified that error appears in the above-indentified patent and that said Letters Patent is hereby corrected as shown below:

<u>Col. 12</u>

In claim 8, line 24, "3-tetramethyl" should be --1,1,3,3-tetramethyl--.

In claim 8, lines 24 and 25, "5-indaneilide" should be --5-indanecarboxanilide--.

In claim 10, line 31, "1,3,3-tetramethyl" should be --1,1,3,3-tetramethyl--.

In claim 12, line 45, "6,7,8-tetrahydro" should be --5,6,7,8-tetrahydro--.

Signed and Sealed this

Thirty-first Day of August, 1993

*Attest:*

BRUCE LEHMAN

*Attesting Officer*      Commissioner of Patents and Trademarks